(12) United States Patent
Harada

(10) Patent No.: US 12,318,068 B2
(45) Date of Patent: Jun. 3, 2025

(54) METHOD OF MOLDING ELEVATOR AND ENDOSCOPE

(71) Applicant: FUJIFILM Corporation, Tokyo (JP)

(72) Inventor: Takashi Harada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 576 days.

(21) Appl. No.: 17/675,886

(22) Filed: Feb. 18, 2022

(65) Prior Publication Data

US 2022/0167829 A1 Jun. 2, 2022

Related U.S. Application Data

(63) Continuation of application No. PCT/JP2020/030873, filed on Aug. 14, 2020.

(30) Foreign Application Priority Data

Aug. 22, 2019 (JP) ................. 2019-151975

(51) Int. Cl.
*A61B 1/00* (2006.01)
*A61B 1/018* (2006.01)
(Continued)

(52) U.S. Cl.
CPC ........ *A61B 1/0011* (2013.01); *A61B 1/00098* (2013.01); *A61B 1/018* (2013.01);
(Continued)

(58) Field of Classification Search
None
See application file for complete search history.

(56) References Cited

U.S. PATENT DOCUMENTS 4,689,184 A * 8/1987 Plummer ............. G02B 6/3865
249/161
5,569,157 A 10/1996 Nakazawa et al.
(Continued)

FOREIGN PATENT DOCUMENTS

| CN | 105982635 A | 10/2016 |
|---|---|---|
| CN | 106102542 A | 11/2016 |

(Continued)

OTHER PUBLICATIONS

Machine language translation of JP2012040258A, Mar. 2012 (Year: 2012).*

(Continued)

*Primary Examiner* — John P Leubecker
(74) *Attorney, Agent, or Firm* — Birch, Stewart, Kolasch & Birch, LLP

(57) ABSTRACT

Provided is a method of molding an elevator and an endoscope, the method making it possible to mold an elevator integrally with an operation wire with a simple operation. A method of molding an elevator (36) is a method of molding an elevator (32) integrally with an operation wire (40), the elevator (32) being to be disposed in a distal-end-portion body (32) of an endoscope (10). The method includes: a step of disposing the operation wire (40) to extend through a cavity (106), which is formed by a first die (102) and a second die (104) that are separable in a separation direction, in a state in which the first die (102) and the second die (104) are mated to each other and in which the separation direction and a wire-axis direction of the operation wire (40) coincide with each other; a step of integrally molding the elevator (36) and the operation wire (40) by injecting a molding material (108), which is a material of the elevator (36), into the cavity (106); and a step of separating the first die (102)

(Continued)

and the second die (104) in the separation direction after molding the elevator.

6 Claims, 17 Drawing Sheets

(51) Int. Cl.
  *B22D 19/04* (2006.01)
  *B22D 19/12* (2006.01)
  *B29C 45/14* (2006.01)
  *B29L 31/00* (2006.01)

(52) U.S. Cl.
  CPC ............. *B22D 19/04* (2013.01); *B22D 19/12* (2013.01); *B29C 45/14467* (2013.01); *B29L 2031/753* (2013.01)

(56) References Cited

U.S. PATENT DOCUMENTS

| | | | |
|---|---|---|---|
| 5,860,913 A | 1/1999 | Yamaya et al. | |
| 5,971,733 A * | 10/1999 | Huang | B29C 45/14639 425/127 |
| 9,748,724 B2 * | 8/2017 | Sato | H01R 43/24 |
| 11,096,558 B2 | 8/2021 | Yamaya | |
| 2001/0003688 A1 * | 6/2001 | Kondo | H01R 13/5216 439/604 |
| 2002/0037140 A1 * | 3/2002 | Ishibashi | G02B 6/3865 264/1.25 |
| 2007/0270638 A1 | 11/2007 | Kitano et al. | |
| 2008/0212908 A1 * | 9/2008 | Mori | F16C 17/107 384/115 |
| 2010/0084774 A1 * | 4/2010 | Liu | B28B 3/021 264/1.25 |
| 2011/0288372 A1 * | 11/2011 | Petersen | A61B 1/00096 600/109 |
| 2012/0319245 A1 * | 12/2012 | Low | H01L 21/565 257/E21.24 |
| 2015/0091206 A1 * | 4/2015 | Sato | B29C 45/14426 425/111 |
| 2016/0270633 A1 | 9/2016 | Iwasaka et al. | |
| 2016/0270635 A1 | 9/2016 | Tanaka et al. | |
| 2017/0000317 A1 | 1/2017 | Iizuka | |
| 2017/0020370 A1 | 1/2017 | Yamaya | |
| 2017/0238789 A1 | 8/2017 | Iizuka et al. | |
| 2018/0092514 A1 | 4/2018 | Yamaya | |
| 2018/0116491 A1 | 5/2018 | Yamaya | |
| 2018/0140171 A1 | 5/2018 | Yamaya | |
| 2018/0153377 A1 * | 6/2018 | Kodama | A61B 1/00101 |
| 2018/0228348 A1 | 8/2018 | Yamaya | |
| 2018/0249894 A1 | 9/2018 | Kolberg et al. | |
| 2018/0317741 A1 | 11/2018 | Yamaya | |
| 2018/0317742 A1 | 11/2018 | Yamaya | |
| 2019/0015172 A1 | 1/2019 | Yamaya | |
| 2019/0117045 A1 | 4/2019 | Hosogoe | |
| 2019/0142242 A1 | 5/2019 | Yamaya | |
| 2019/0223692 A1 * | 7/2019 | Nakagawa | B21F 15/00 |
| 2020/0008658 A1 | 1/2020 | Hayakawa | |
| 2020/0352423 A1 | 11/2020 | Hayakawa | |
| 2022/0167835 A1 | 6/2022 | Harada | |

FOREIGN PATENT DOCUMENTS

| | | |
|---|---|---|
| CN | 106999007 A | 8/2017 |
| CN | 107847114 A | 3/2018 |
| CN | 108024700 A | 5/2018 |
| JP | 6-315459 A | 11/1994 |
| JP | 6-319692 A | 11/1994 |
| JP | 7-148104 A | 6/1995 |
| JP | 7-163514 A | 6/1995 |
| JP | 8-252210 A | 10/1996 |
| JP | 9-75300 A | 3/1997 |
| JP | 9-103415 A | 4/1997 |
| JP | 10-99266 A | 4/1998 |
| JP | 11-299728 A | 11/1999 |
| JP | 2001-249250 A | 9/2001 |
| JP | 2010-273727 A | 12/2010 |
| JP | 2012-40258 A | 3/2012 |
| JP | 2012-51008 A | 3/2012 |
| JP | 2016-174819 A | 10/2016 |
| JP | 2018-68834 A | 5/2018 |
| JP | 2018-517440 A | 7/2018 |
| WO | WO2016/027574 A1 | 2/2016 |
| WO | WO 2018/016484 A1 | 1/2018 |

OTHER PUBLICATIONS

Chinese Office Action and Search Report for corresponding Chinese Application No. 202080057802.X, dated Jan. 12, 2024, with an English translation.
International Preliminary Report on Patentability and Written Opinion of the International Searching Authority (Forms PCT/IB/326, PCT/IB/373, and PCT/ISA/237) for International Application No. PCT/JP2020/030874, dated Mar. 3, 2022, with an English translation.
International Search Report (Form PCT/ISA/210) for International Application No. PCT/JP2020/030874, dated Oct. 20, 2020, with an English translation.
Japanese Notice of Reasons for Refusal for corresponding Japanese Application No. 2021-540764, dated May 22, 2023, with an English translation.
International Preliminary Report on Patentability (Form PCT/IPEA/409) for International Application No. PCT/JP2020/030873, dated Jul. 7, 2021, with an English translation.
International Search Report (Form PCT/ISA/210) for International Application No. PCT/JP2020/030873, dated Oct. 20, 2020, with an English translation.
U.S. Office Action for U.S. Appl. No. 17/675,133, dated Aug. 28, 2024.
Japanese Decision of Refusal for corresponding Japanese Application No. 2021-540764, dated Oct. 23, 2023, with an English translation.
Chinese Office Action and Search Report for Chinese Application No. 202080057798.7, dated Oct. 14, 2024, with an English translation.

\* cited by examiner

METHOD OF MOLDING ELEVATOR AND ENDOSCOPE

CROSS-REFERENCE TO RELATED APPLICATIONS

The present application is a Continuation of PCT International Application No. PCT/JP2020/030873 filed on Aug. 14, 2020 claiming priority under 35 U.S.C. § 119(a) to Japanese Patent Application No. 2019-151975 filed on Aug. 22, 2019. Each of the above applications is hereby expressly incorporated by reference, in its entirety, into the present application.

BACKGROUND OF THE INVENTION

1. Field of the Invention

The present invention relates to a method of molding an elevator and to an endoscope, and, in particular, to a method of molding an elevator in which the elevator and an operation wire are directly coupled, and to an endoscope including a molded elevator.

2. Description of the Related Art

With an endoscope, a treatment tool of an appropriate type is inserted from a treatment-tool insertion port that is formed in an operation section, and the treatment tool is used for treatment by leading out the treatment tool to the outside from a treatment-tool lead-out port that is formed in a distal end portion of an insertion section. For example, a treatment tool such as a guidewire or an imaging cannula is used with a duodenum scope. A treatment tool such as a puncture needle is used with an ultrasonic endoscope. A treatment tool such as forceps, a snare, or the like is used with other straight-viewing endoscopes and oblique-viewing endoscopes. In order to treat a desirable position in a subject with such a treatment tool, it is necessary to change the lead-out direction at the distal end portion. Therefore, an elevator for changing the lead-out direction of the treatment tool is provided in the distal end portion of the insertion portion. Moreover, in the endoscope, a treatment-tool-elevating mechanism for displacing the position of the elevator between an elevated position and a lowered position is provided.

As the treatment-tool-elevating mechanism, a wire-pulling-type (open-type) mechanism, in which the distal end of an operation wire is directly attached to an elevator, is known. The mechanism, in which the proximal end of the operation wire is coupled to an operation lever provided in an operation section, rotates the elevator around a rotation shaft when the operation lever is pushed or pulled via the operation lever to change the position of the elevator between the elevated position and the lowered position.

As a method of directly attaching the distal end of an operation wire to an elevator, a method of brazing or welding the elevator and the operation wire to each other or a method of attaching the distal end by crimping is used.

As a method of molding an elevator, JP1994-315459A (JP-H06-315459A) describes that a forceps elevating wire and a forceps elevator are integrally molded. WO2016/27574A describes that a distal end portion of a pulling-pressing member is fixed to an elevator by using soler or the like. JP1999-299728A (JP-H11-299728A) describes that a wire insertion path, for inserting an operation wire, is also integrally molded when molding a treatment tool elevator.

SUMMARY OF THE INVENTION

In the forceps elevator (elevator) described in JP1994-299728A (JP-H06-315459A), a forceps elevating wire (operation wire) is inserted into the elevator from a side surface of the forceps elevator, and, because the insertion direction of the forceps elevating wire and the axial direction of the forceps elevating wire are different, it is necessary to bend the forceps elevating wire during molding, and the manufacturing process is complicated. Also regarding an elevator (elevator) described in WO2016/27574A, it is necessary to bend the pulling-pressing member (operation wire).

Moreover, in WO2016/27574A, the pulling-pressing member and the elevator are fixed by using solder, and the pulling-pressing member and the elevator are not integrally molded. Also in a treatment tool elevating device described in JP1999-299728A (JP-H11-299728A), although the wire insertion path to be formed in the treatment tool elevator is formed by integral molding or the like, the operation wire and the treatment tool elevator are not integrally formed.

The present invention has been made against such a background, and an object thereof is to provide a method of molding an elevator and an endoscope, the method making it possible to mold an elevator integrally with an operation wire with a simple operation.

In order to achieve the object of the present invention, a method of molding an elevator endoscope according to the present invention is a method of molding an elevator integrally with an operation wire, the elevator being to be disposed in a distal-end-portion body provided on a distal end side of an insertion section of an endoscope. The method includes: a step of disposing the operation wire to extend through a cavity, which is formed by a first die and a second die that are separable in a separation direction, in a state in which the first die and the second die are mated to each other and in which the separation direction and a wire-axis direction of the operation wire coincide with each other; a step of integrally molding the elevator and the operation wire by injecting a molding material, which is a material of the elevator, into the cavity; and a step of separating the first die and the second die in the separation direction after molding the elevator.

In order to achieve an object of the present invention, a method of molding an elevator endoscope according to the present invention is a method of molding an elevator integrally with an operation wire, the elevator being to be disposed in a distal-end-portion body provided on a distal end side of an insertion section of an endoscope. The method includes: a step of disposing the operation wire to extend through a cavity, which is formed by a first die and a second die that are separable in a separation direction, in a state in which the first die and the second die are mated to each other and in which a direction perpendicular to the separation direction and a wire-axis direction of the operation wire coincide with each other; a step of integrally molding the elevator and the operation wire by injecting a molding material, which is a material of the elevator, into the cavity; and a step of separating the first die and the second die in the separation direction after molding the elevator.

To achieve an object of the present invention, an endoscope according to the present invention includes an operation section having an operation member; an insertion section that is provided on a distal end side of the operation section; a distal-end-portion body that is provided on the distal end side of the insertion section; an elevator that is provided in the distal-end-portion body and that is rotatably disposed; and an operation wire that rotates the elevator by being pushed and pulled in accordance with a movement of the operation member. The elevator is an integrally molded body that is molded integrally with the operation wire by using a first die and a second die that are separable in a wire-axis direction of the operation wire.

With the present invention, it is possible to facilitate disposition of an operation wire in a cavity and to easily take out a molded elevator by separating the first die and the second die in the separation direction.

DESCRIPTION OF THE PREFERRED EMBODIMENTS

Hereafter, a method of molding an elevator and an endoscope according to the present invention will be described with reference to the drawings.

Figure 1:
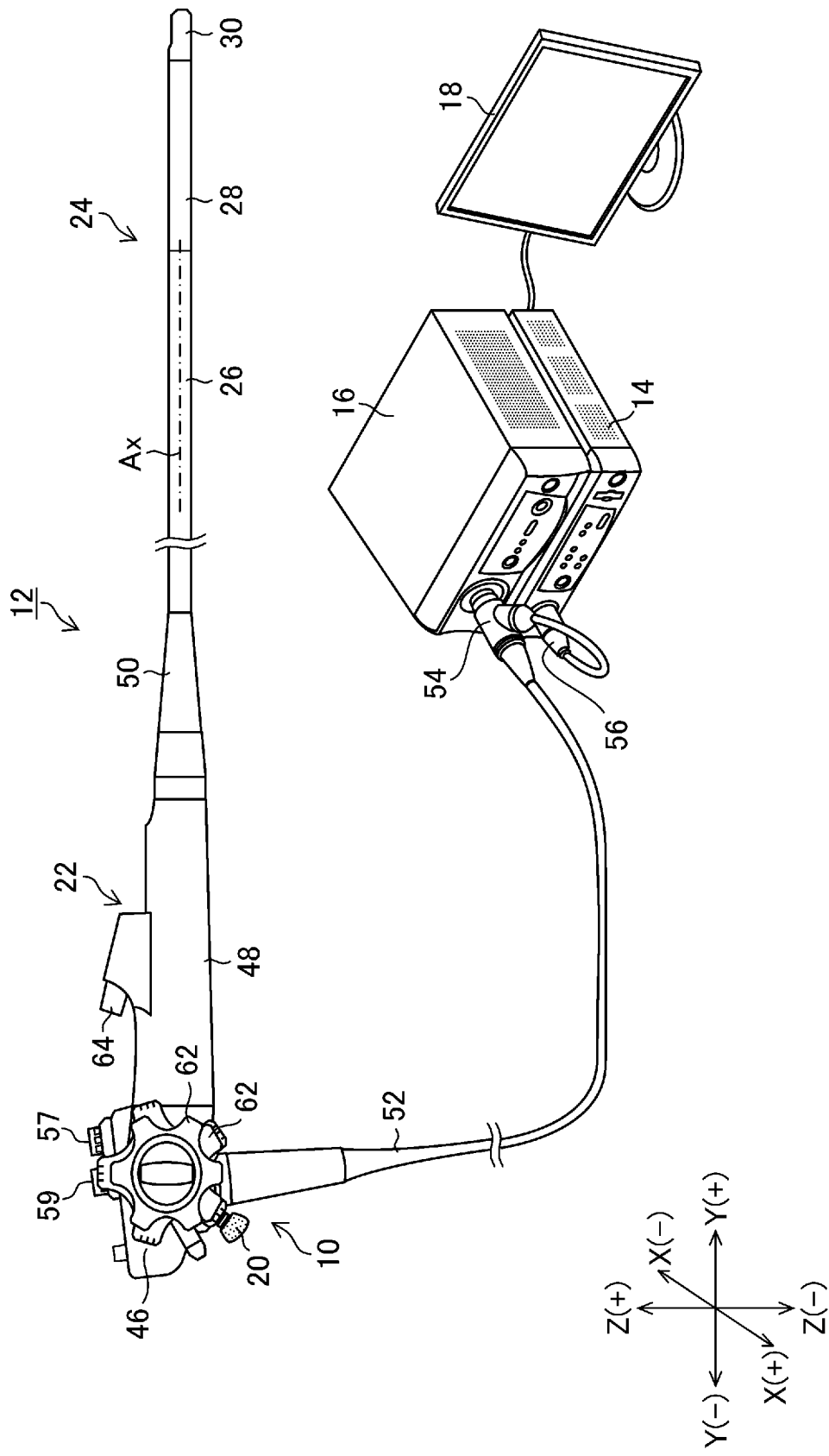
FIG. 1 illustrates the configuration of an endoscope system including an endoscope.

FIG. 1 illustrates the configuration of an endoscope system including an endoscope molded by using a method of molding an elevator according to the present invention. An endoscope system 12 includes an endoscope 10, a processor device 14, a light source device 16, and a display 18.

The endoscope 10 includes: an operation section 22 in which an elevating operation lever 20, which is an operation member, is provided; and an insertion section 24, which is provided on the distal end side of the operation section 22 and which is to be inserted into a subject.

The insertion section 24 has a longitudinal axis Ax extending from the proximal end toward the distal end; and includes a flexible portion 26, a bending portion 28, and a distal end portion 30, sequentially from the proximal end toward the distal end. First, schematic configuration of the distal end portion 30 will be described, and then detailed configuration of the distal end portion 30 will be described.

Figure 2:
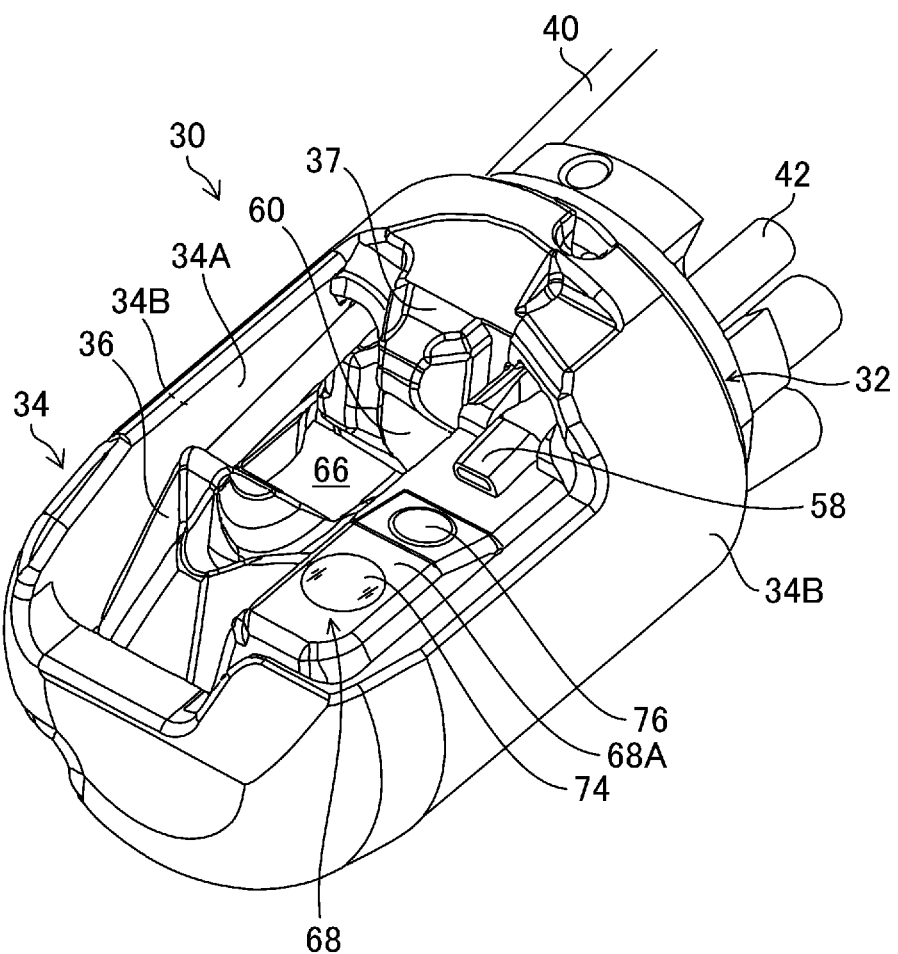
FIG. 2 is an enlarged perspective view of a distal end portion of the endoscope.
Figure 2:
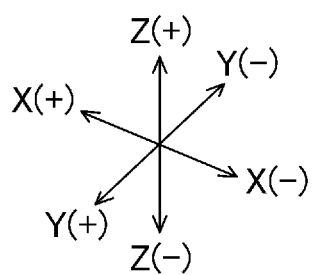

FIG. 2 is an enlarged perspective view of the distal end portion 30. Here, the endoscope 10 according to the embodiment (see FIG. 1) is, for example, a side-viewing endoscope used as a duodenum scope, and the distal end portion 30 of FIG. 2 has the configuration of a side-viewing endoscope.

Figure 3:
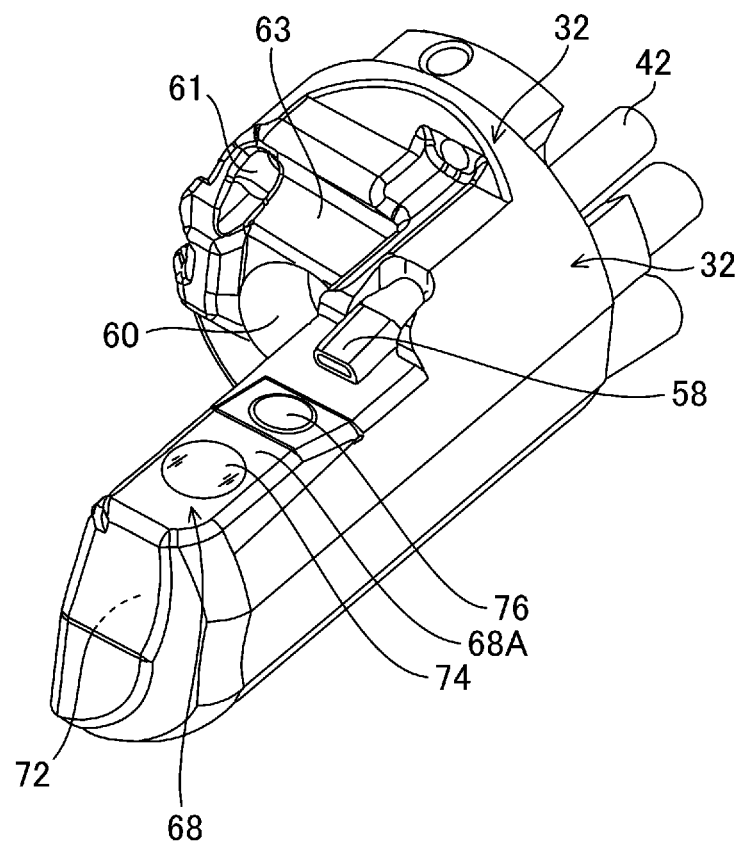
FIG. 3 is a perspective view of a distal-end-portion body illustrated in FIG. 2.
Figure 3:
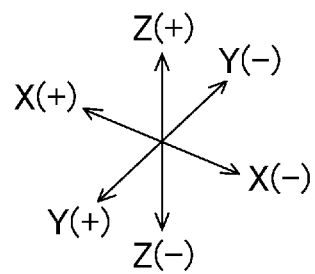
Figure 4:
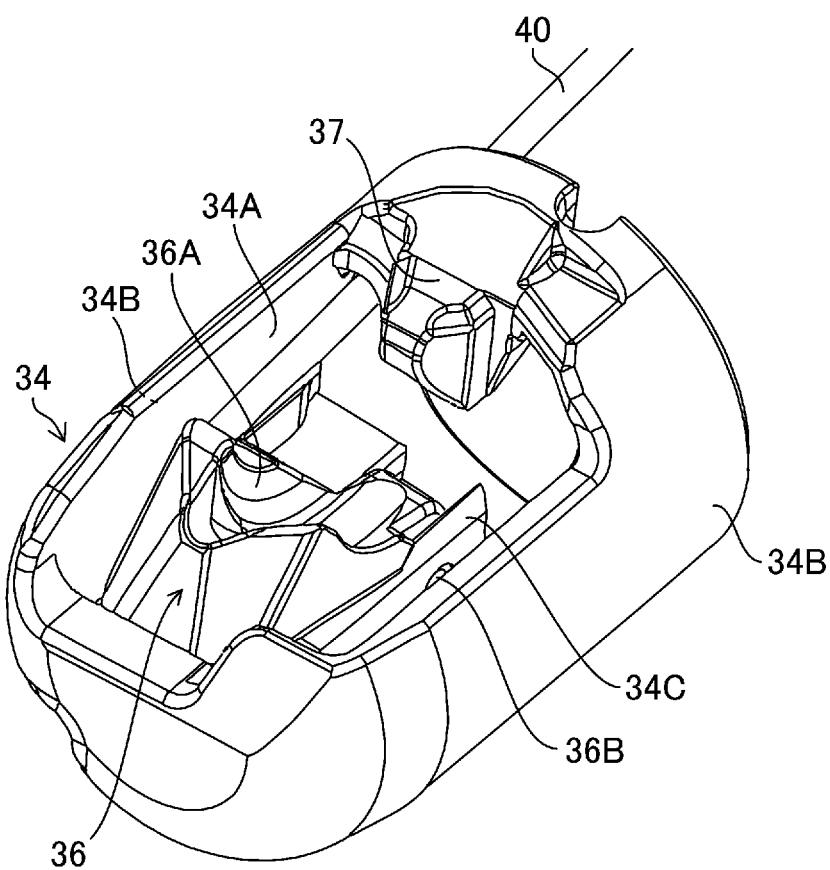
FIG. 4 is a perspective view of a cap illustrated in FIG. 2.

FIG. 3 is a perspective view of a distal-end-portion body 32 of the distal end portion 30. FIG. 4 is a perspective view of a cap 34 of the distal end portion 30. As illustrated in FIG. 2, the distal end portion 30 has the distal-end-portion body 32 and the cap 34. The cap 34 is removably attached to the distal-end-portion body 32. The distal-end-portion body 32 is provided on the distal end side of the insertion section 24 (see FIG. 1). In the distal-end-portion body 32, an elevator 36, which has a treatment-tool guiding surface 36A described below, is provided. FIGS. 2 and 4 illustrate a state in which the elevator 36 is in a lowered position.

FIG. 2 also illustrates various elements that are placed inside the insertion section 24 of the endoscope 10 (see FIG. 1). To be specific, provided are the following: the elevator 36 for performing, on a distal end portion of a treatment tool (not shown), an operation of changing the lead-out direction of the distal end portion of the treatment tool that is led out from the distal-end-portion body 32; an operation wire 40; and an air/water supply tube 42. The operation wire 40 is directly coupled to the elevator 36 and is an integrally molded body in which the elevator 36 and the operation wire 40 are integrally molded when molding the elevator 36. Although not illustrated in FIG. 2, the following contents are also provided: a treatment tool channel leading to the distal-end-portion body 32; an angle wire for performing an operation of changing the bending direction of the bending portion 28 (see FIG. 1); a signal cable for transmitting an image signal; a light guide for transmitting illumination light; and the like.

In the present specification, a three-dimensional orthogonal coordinate system having a triaxial direction (X-axis direction, Y-axis direction, Z-axis direction) will be used for description. That is, as seen from the operation section 22 toward the distal end portion 30, when the direction in which the treatment tool (not shown) is led out by the elevator 36 is defined as the upward direction, the upward direction is defined as the Z(+) direction, and the downward direction, which is opposite to the upward direction, is defined as the Z(−) direction. The forward direction at this time (direction toward the distal end side in the direction of the longitudinal axis Ax of the insertion section 24) is defined as the Y(+) direction, and the backward direction (direction toward the proximal end side in the direction of the longitudinal axis Ax of the insertion section 24) is defined as the Y(−) direction. The Y-axis direction, including the Y(+) direction and the Y(−) direction, is parallel to the direction of the longitudinal axis Ax of the insertion section 24. The Z-axis direction is a direction perpendicular to the direction of the longitudinal axis Ax. The X-axis direction is a direction perpendicular to the Z-axis direction.

Referring back to FIG. 1, the operation section 22 as a whole has a substantially cylindrical shape. The operation section 22 includes an operation section body 46 on which the elevating operation lever 20 is rotatably provided, and a grip portion 48 that is continuously connected to the operation section body 46. A proximal end portion of the insertion section 24 is provided on the distal end side of the grip portion 48 via a breakage preventing tube 50. The grip portion 48 is a portion to be gripped by an operator when the operator operates the endoscope 10.

The operation section body 46 is equipped with a universal cable 52. A light source connector 54 is provided on the distal end side of the universal cable 52. An electric connector 56 branches from the light source connector 54. The electric connector 56 is connected to the processor device 14, and the light source connector 54 is connected to the light source device 16.

On the operation section body 46, an air/water supply button 57 and a suction button 59 are arranged side by side. When the air/water supply button 57 is operated, air and water are supplied to the air/water supply tube 42 of FIG. 2, and the air and water can be ejected from an air/water supply nozzle 58 provided in the distal-end-portion body 32. The air/water supply button 57 of FIG. 1 is operated in two steps. With an operation in the first step, air is supplied to the air/water supply tube 42. With an operation in the second step, water is supplied to the air/water supply tube 42.

When the suction button 59 of FIG. 1 is operated, a bodily fluid such as blood can be sucked from a treatment-tool lead-out port 60, which is provided in the distal-end-portion body 32 of FIG. 2, through a treatment tool channel (not shown).

As illustrated in FIG. 1, a pair of angle knobs 62, which are used to for the operation of bending the bending portion 28, is disposed on the operation section body 46. The pair of angle knobs 62 are coaxially rotatable.

The elevating operation lever 20 is rotatable coaxially with the angle knobs 62. The elevating operation lever 20 is rotated by a hand of an operator who grips the grip portion 48. When the elevating operation lever 20 is rotated, the operation wire 40 of FIG. 2 is pushed or pulled in accordance with a movement of the elevating operation lever 20. Due to such an operation on the operation wire 40, the posture of the elevator 36, which is coupled to the distal end side of the operation wire 40, is changed between the lowered position illustrated in FIG. 2 and the elevated position (not shown).

As illustrated in FIG. 1, the grip portion 48 of the operation section 22 includes a treatment-tool insertion port 64 for inserting a treatment tool. A treatment tool (not shown), which is inserted from the treatment-tool insertion port 64 with the distal end portion thereof being a leading end portion, is inserted into the treatment tool channel (not shown), and is led to the outside from the treatment-tool lead-out port 60 provided in the distal-end-portion body 32.

As illustrated in FIG. 1, the flexible portion 26 of the insertion section 24 has a helical tube (not shown) that is formed by helically winding a thin metal strip having elasticity. The flexible portion 26 is formed by covering the outside of this helical tube with a tubular mesh member, which is made of a braided metal wire, and by covering the outer peripheral surface of the mesh member with an outer covering made of a resin.

The bending portion 28 of the insertion section 24 has a structure such that a plurality of angle rings (not shown) are unrotatably coupled to each other. The bending portion 28 is formed by covering the outer periphery of this structure with a tubular mesh member made of a braided metal wire, and by covering the outer peripheral surface of the mesh member with a tubular outer covering made of rubber. For example, four angle wires (not shown) are placed from the bending portion 28, which is configured in this way, to the angle knobs 62. When the angle knobs 62 are rotated, these angle wires are pushed or pulled, and thereby the bending portion 28 is bent in the up-down direction and in the left-right direction.

The endoscope 10 according to the embodiment is, for example, a side-viewing endoscope that is used as a duodenum scope, and the insertion section 24 is inserted into a subject through the oral cavity. The insertion section 24 is inserted from the esophagus to the duodenum through the stomach, and a predetermined operation such as a predetermined test or treatment is performed.

Examples of a treatment tool used with the endoscope 10 according to the embodiment include: biopsy forceps having a cup, which can obtain living tissue, at a distal end portion; an endoscopic sphincterotomy (EST) knife; and an imaging cannula.

Next, referring to FIGS. 2, 3, and 4, the structure of the distal end portion 30 will be described.

As illustrated in FIG. 2, the distal end portion 30 includes the distal-end-portion body 32 and the cap 34 that is removably attached to the distal-end-portion body 32. As illustrated in FIG. 3, the distal-end-portion body 32 has a partition wall 68 that protrudes in the Y(+) direction. When the cap 34 is attached to the distal-end-portion body 32, an elevator housing space 66 is formed by the partition wall 68 of the distal-end-portion body 32 and wall portions 34B of the cap 34. The elevator housing space 66 is disposed at a position in the X(+) direction of the partition wall 68 and in the Y(+) direction of the treatment-tool lead-out port 60. The distal-end-portion body 32 is made of an anticorrosive metal material.

As illustrated in FIGS. 2 and 3, in an upper surface 68A on the Z(+) side of the partition wall 68, an illumination window 74 and an observation window 76 are placed adjacent to each other in the Y direction. The observation window 76 enables observation of a field of view in the Z(+) direction, in which the elevator housing space 66 opens.

The air/water supply nozzle 58 is provided on the distal-end-portion body 32 toward the observation window 76. The observation window 76 is cleaned with air and water ejected from the air/water supply nozzle 58.

As illustrated in FIG. 3, the partition wall 68 includes an optical-system housing chamber 72 inside thereof. The optical-system housing chamber 72 houses an illumination unit (not shown) and an imaging unit (not shown). The illumination unit includes an illumination lens (not shown), which is disposed on the optical-system housing chamber 72 side of the illumination window 74, and a light guide (not shown), which is disposed so that a distal end surface thereof faces the illumination lens. The light guide is placed into the universal cable 52 from the insertion section 24 of the endoscope 10 (see FIG. 1) through the operation section 22. A proximal end of the light guide is connected to the light source connector 54. When the light source connector 54 is connected to the light source device 16, irradiation light from the light source device 16 is transmitted to the illumination lens through the light guide. A field of view in the Z(+) direction is irradiated with irradiation light from the illumination window 74.

The imaging unit includes an imaging optical system (not shown), which is placed inside the observation window 76, and an image pick-up element (not shown) of a complementary metal oxide semiconductor (CMOS) type or a charge coupled device (CCD) type. A distal end of a signal cable (not shown) is connected to the image pick-up element. The signal cable is placed into the universal cable 52 from the insertion section 24 of the endoscope 10 (see FIG. 1) through the operation section 22. A proximal end of the signal cable is connected to the electric connector 56. When the electric connector 56 is connected to the processor device 14, an image pick-up signal of a subject image obtained by the imaging unit is transmitted to the processor device 14 through the signal cable. The image pick-up signal is image-processed by the processor device 14 and then displayed on the display 18 as a subject image.

The distal-end-portion body 32 has a stopper portion 63 on the proximal end side thereof. The stopper portion 63 engages with a stopper-target portion (described below) that is provided on a surface of a contact member 37 on the proximal end side. In the distal-end-portion body 32, a through-hole 61, for inserting the operation wire 40 (not shown) therethrough, is formed.

As illustrated in FIG. 4, the cap 34 includes the wall portion 34B that has a substantially tubular shape whose distal end side is sealed. In a part of the outer peripheral surface of the cap 34, an open window 34A having a substantially rectangular shape is defined by the wall portion 34B. A bearing 34C, which extends in the Y(+) direction, is formed inside the cap 34. The bearing 34C has a plate-like shape having a height in the Z(+) direction. The cap 34 is made of an elastic material that is, for example, a rubber material, such as fluorocarbon rubber or silicone rubber, or a resin material, such as polysulfone or polycarbonate.

A rotation shaft 36B of the elevator 36 is supported in a through-hole (not shown) of the bearing 34C. The rotation shaft 36B is a rod-shaped member having a length in the X-axis direction perpendicular to the bearing 34C. The rotation shaft 36B is integrally molded with the elevator 36 when molding the elevator 36. Alternatively, the rotation shaft 36B may be installed by forming a through-hole (not shown) in the elevator 36 and by inserting a rod-shaped member into the through-hole.

The operation wire 40 is attached by being directly coupled to the elevator 36 as described below. The operation wire 40 is attached to a position adjacent to the treatment-tool guiding surface 36A on the distal end side of the elevator 36.

In the present embodiment, the elevator 36 is attached to the cap 34 illustrated in FIG. 4, and the cap 34 with the elevator 36 is used as a single component as a whole. The operation wire 40 is coupled to the elevator 36.

The open window 34A of the cap 34 opens in the Z(+) direction. That is, the opening direction of the open window 34A of the cap 34 is a direction that is perpendicular to the direction of the longitudinal axis Ax of the insertion section and that is perpendicular to the axial direction of the rotation shaft 36B (X direction).

The cap 34 includes the contact member 37 that is integrally molded with the wall portion 34B. The contact member 37 is made of a resin material. The contact member 37 is disposed on the proximal end side (in the Y(−) direction) of the open window 34A. The contact member 37 as a whole protrudes in the Y(+) direction. The phrase "integrally mold" means integrally molding a product (the cap 34 and the contact member 37) at the same a time as joining of members, without using adhesives or mechanical joint.

The cap 34, including the operation wire 40 and the elevator 36, is removed from the distal-end-portion body 32 after a treatment using the endoscope 10 is finished, and, for example, is thrown away as a disposable item.

When the cap 34 is attached to the distal-end-portion body 32, as illustrated in FIG. 2, the cap 34 forms the elevator housing space 66, and the open window 34A opens in the Z(+) direction. The treatment-tool lead-out port 60 of the distal-end-portion body 32 communicates with the open window 34A through the elevator housing space 66. The contact member 37 is positioned in the Z(+) direction with respect to the treatment-tool lead-out port 60, and the contact member 37 is provided at a position at which the contact member 37 faces the treatment-tool guiding surface 36A when the elevator 36 is in the elevated position.

(Method of Molding Elevator)

Figure 5:
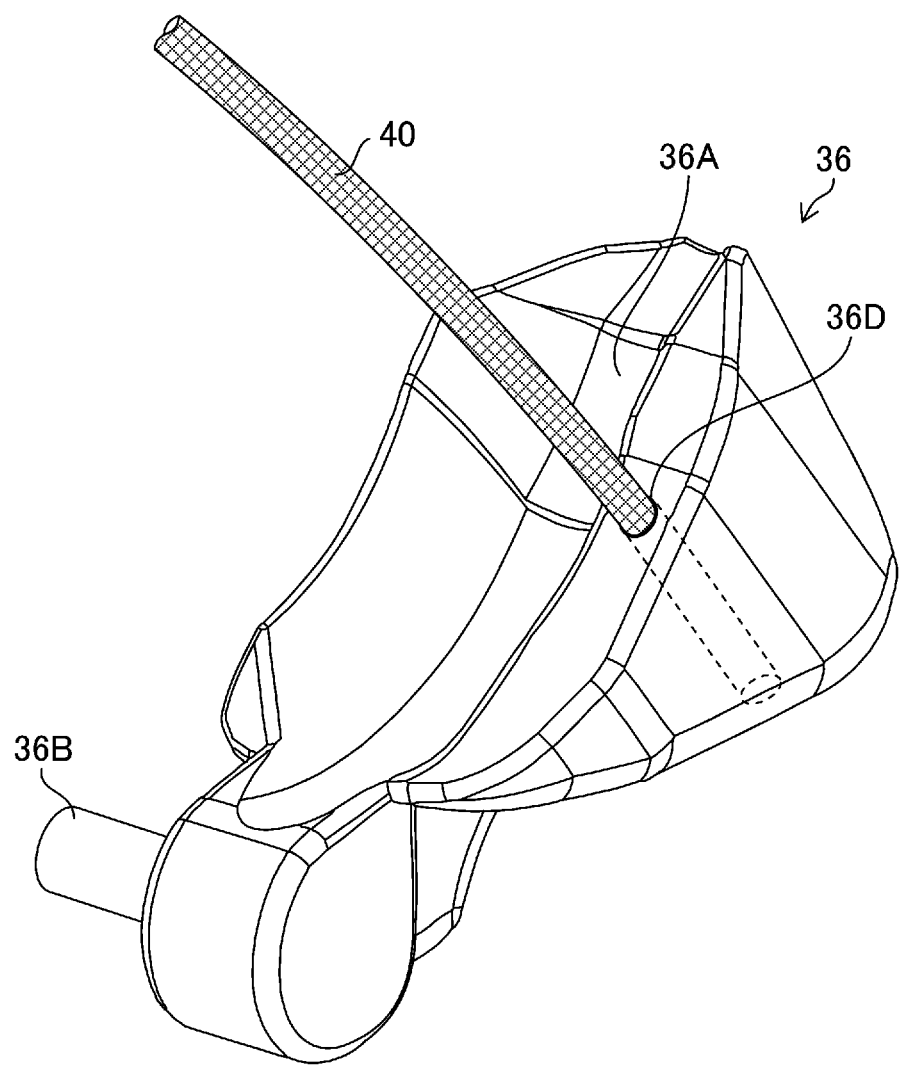
FIG. 5 is a perspective view an elevator and an operation wire.

Next, a method of molding an elevator will be described. FIG. 5 is a perspective view of an elevator molded by using a method of molding an elevator according to the present invention. The operation wire 40 is directly connected to the elevator 36, and the elevator 36 and the operation wire 40 are integrally molded when molding the elevator 36.

First Embodiment

A method of molding an elevator according to a first embodiment will be described. The method of molding an elevator according to the first embodiment is a method of continuously molding the elevator 36.

FIGS. 6 to 10 illustrate the method of molding an elevator according to the first embodiment, and FIGS. 6, 7, 8, and 10 are each a sectional plan view cut at the position of the operation wire 40. The structure of the inside of a cavity 106 of a first die 102 and a second die 104 is omitted for simplicity of the drawings.

Molding of the elevator 36 is performed by using a die 100 that is composed of the first die 102 and the second die 104. The first die 102 and the second die 104 are separable in a separation direction indicated by an arrow A (hereafter, referred to as "separation direction A"). Moreover, the second die 104 is separable into a first member 104A and a second member 104B in a separation direction indicated by an arrow B (hereafter, referred to as "separation direction B"). By mating the first die 102 and the second die 104 to each other, the cavity 106 corresponding to the elevator 36 is formed inside of the first die 102 and the second die 104. The first die 102 has a through-hole 110A for inserting the operation wire 40 into the cavity 106. The second die 104 has, at a position facing the through-hole 110A of the first die 102, a through-hole 110B for inserting the operation wire 40 from the cavity 106 to the outside of the second die 104. The through-hole 110B of the second die 104 is formed of a groove in the first member 104A and a groove in the second member 104B.

Figure 6:
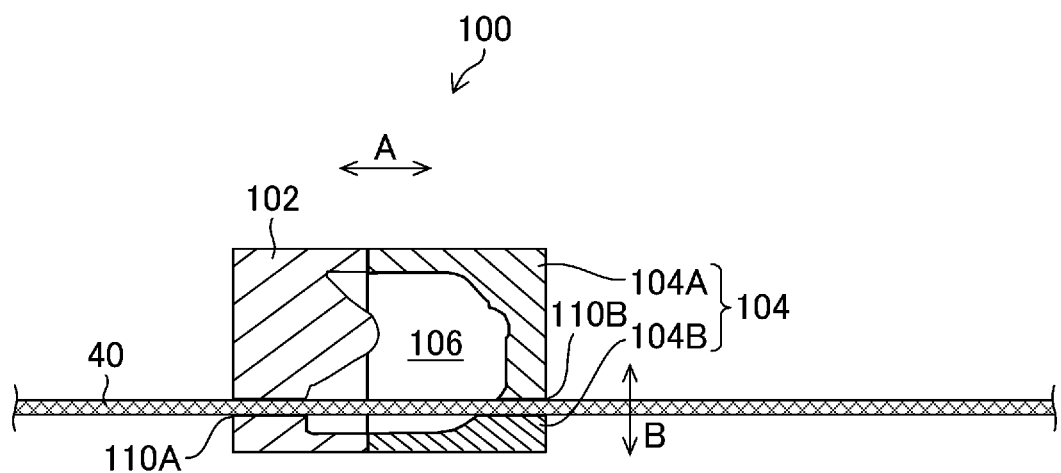
FIG. 6 illustrates a method of molding an elevator according to a first embodiment.

As illustrated in FIG. 6, when molding the elevator 36, the first die 102 and the second die 104 are mated to each other. The operation wire 40 extends through the through-hole 110A provided in the first die 102, is disposed to extend through the cavity 106, and is made to extend through the through-hole 110B of the second die 104. The operation wire 40 is disposed so as to pass through the cavity 106 from the first die 102 side to the second die 104 side. At this time, the operation wire 40 and the die 100 are disposed in a state in which the wire-axis direction of the operation wire 40 and the separation direction A coincide with each other. The phrase "the wire-axis direction of the operation wire 40 and the separation direction A coincide with each other" is not limited to the meaning that the wire-axis direction of the operation wire 40 and the separation direction A completely coincide with each other, and may include a displacement to such a degree that, when taking out the elevator 36, the elevator 36 can be taken out by moving the elevator 36 in the same direction as the separation direction A.

Figure 7:
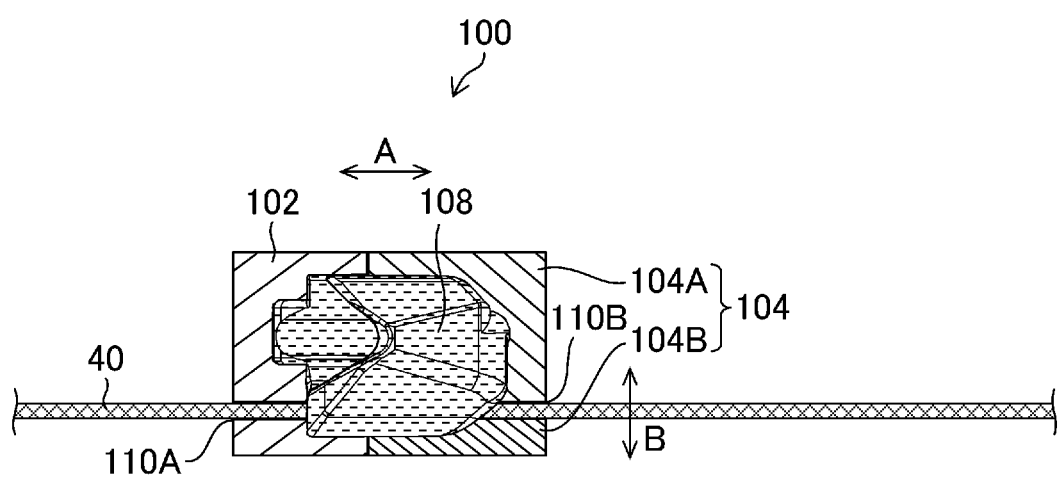
FIG. 7 illustrates the method of molding an elevator according to the first embodiment.

Next, as illustrated in FIG. 7, a molding material 108, which is the material of the elevator 36, is injected into the cavity 106. A resin can be used as the molding material 108, and the cavity 106 is filled with a molten resin. As the resin, for example, polyether ether ketone (PEEK) can be used. Alternatively, a metal may be used as the molding material 108, and the cavity 106 may be filled with a molten metal by metal injection molding (MIM).

When PEEK is used as the material of the elevator 36, preferably, stainless steel (SUS, whose melting point is about 1400° C.) is used as the material of the operation wire 40, because the molding temperature of the elevator 36 is higher than equal to 350° C. and lower than or equal to 400° C. When a metal is used as the material of the elevator 36, preferably, tungsten (whose melting point is about 3400° C.) is used as the material of the operation wire 40, because the molding temperature of the elevator 36 is higher than equal to 1200° C. and lower than or equal to 1400° C.

After filling the cavity 106 with the molding material 108, the molding material 108 is cooled to be solidified, and thus the elevator 36 in which the operation wire 40 is disposed is formed.

Figure 8:
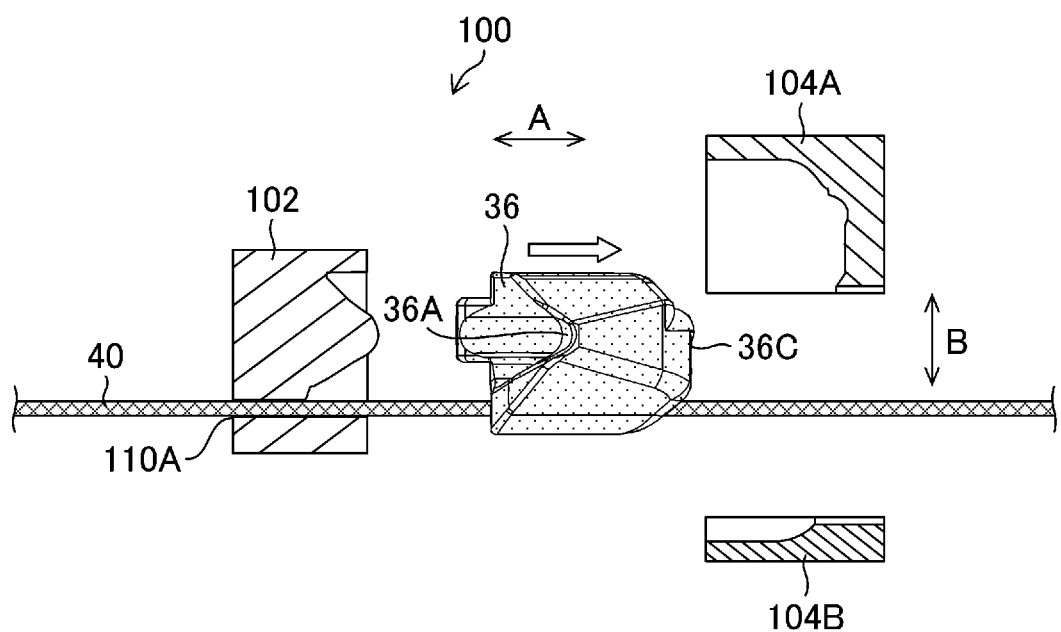
FIG. 8 illustrates the method of molding an elevator according to the first embodiment.

After molding the elevator 36, as illustrated in FIG. 8, the first die 102 and the second die 104 are separated in the separation direction A, and the second die 104 is separated into the first member 104A and the second member 104B in the separation direction B. Because the separation direction A of the first die 102 and the second die 104 coincide with the wire-axis direction of the operation wire 40, it is possible to separate the elevator 36 from the first die 102 without bending the operation wire 40 by moving the second die in the wire-axis direction of the operation wire 40 together with the elevator 36.

Because the elevator 36 is moved together with the second die 104 in the same direction as the separation direction A, it is possible to separate the elevator 36 from the first die 102 in a state in which the first die 102 is fixed. The elevator 36 separated from the first die 102 can be pulled out in the wire-axis direction of the operation wire 40 from a space between the first member 104A and the second member 104B that have been separated.

Figure 9:
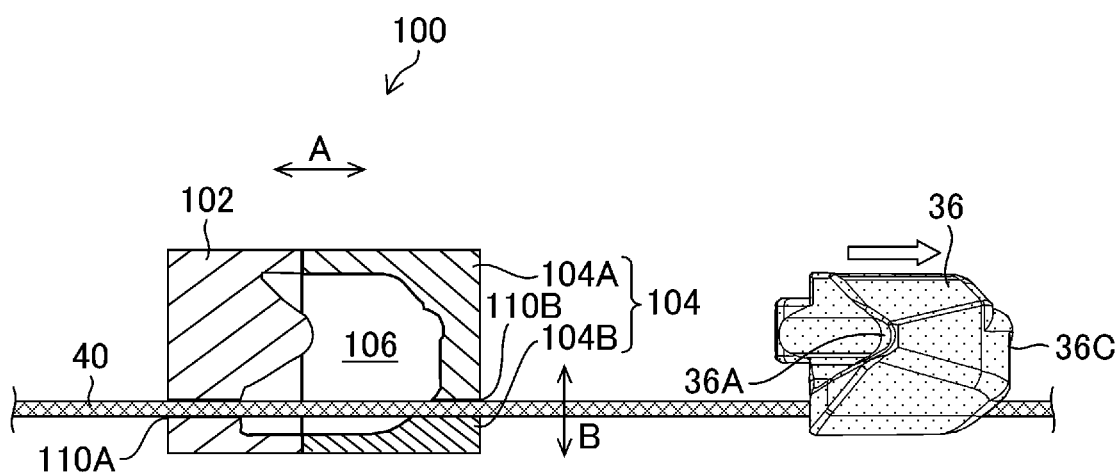
FIG. 9 illustrates the method of molding an elevator according to the first embodiment.
Figure 10:
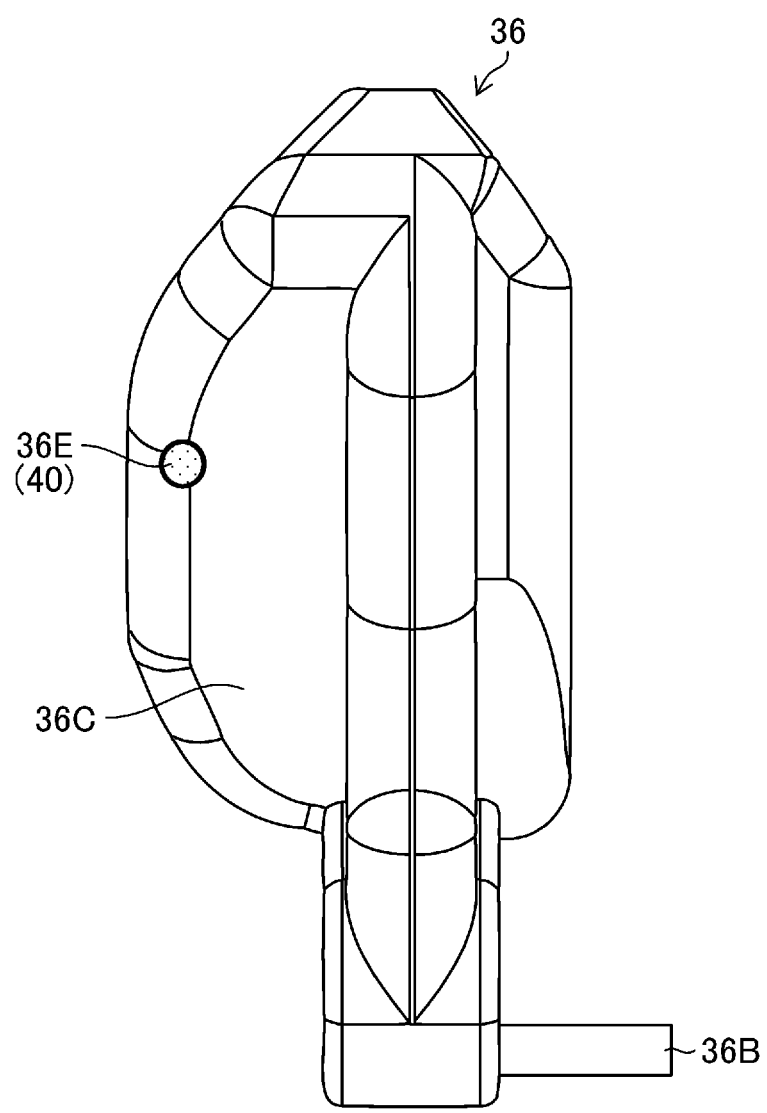
FIG. 10 illustrates the elevator as seen from the back surface side.

As illustrated in FIG. 9, after separating the elevator 36 from the die 100, the die 100 is mated again. After removing the elevator 36 from the die 100, the operation wire 40 is cut. The operation wire 40 on a side of the treatment-tool guiding surface 36A of the elevator 36 is cut to have a length connectable with the elevating operation lever 20 illustrated in FIG. 1. The operation wire 40 protruding from a side of the back surface 36C of the elevator 36 opposite to the treatment-tool guiding surface 36A is cut along the back surface 36C. FIG. 10 is a view as seen from the side of a back surface 36C of the elevator 36. On the side of the back surface 36C of the elevator 36, an exposed portion 36E where the operation wire 40 is exposed due to cutting of the protruding operation wire 40 is formed. As illustrated in FIG. 5, on the side the treatment-tool guiding surface 36A of the elevator 36, the operation wire 40 is directly connected at a connection portion 36D provided in a side portion of the treatment-tool guiding surface 36A.

The die 100, from which the elevator 36 has been pulled out and which has been mated, is returned to the step of FIG. 6, the cavity 106 is filled with the molding material 108 for molding the elevator 36, and continuous molding of the elevator 36 is performed.

Figure 11:
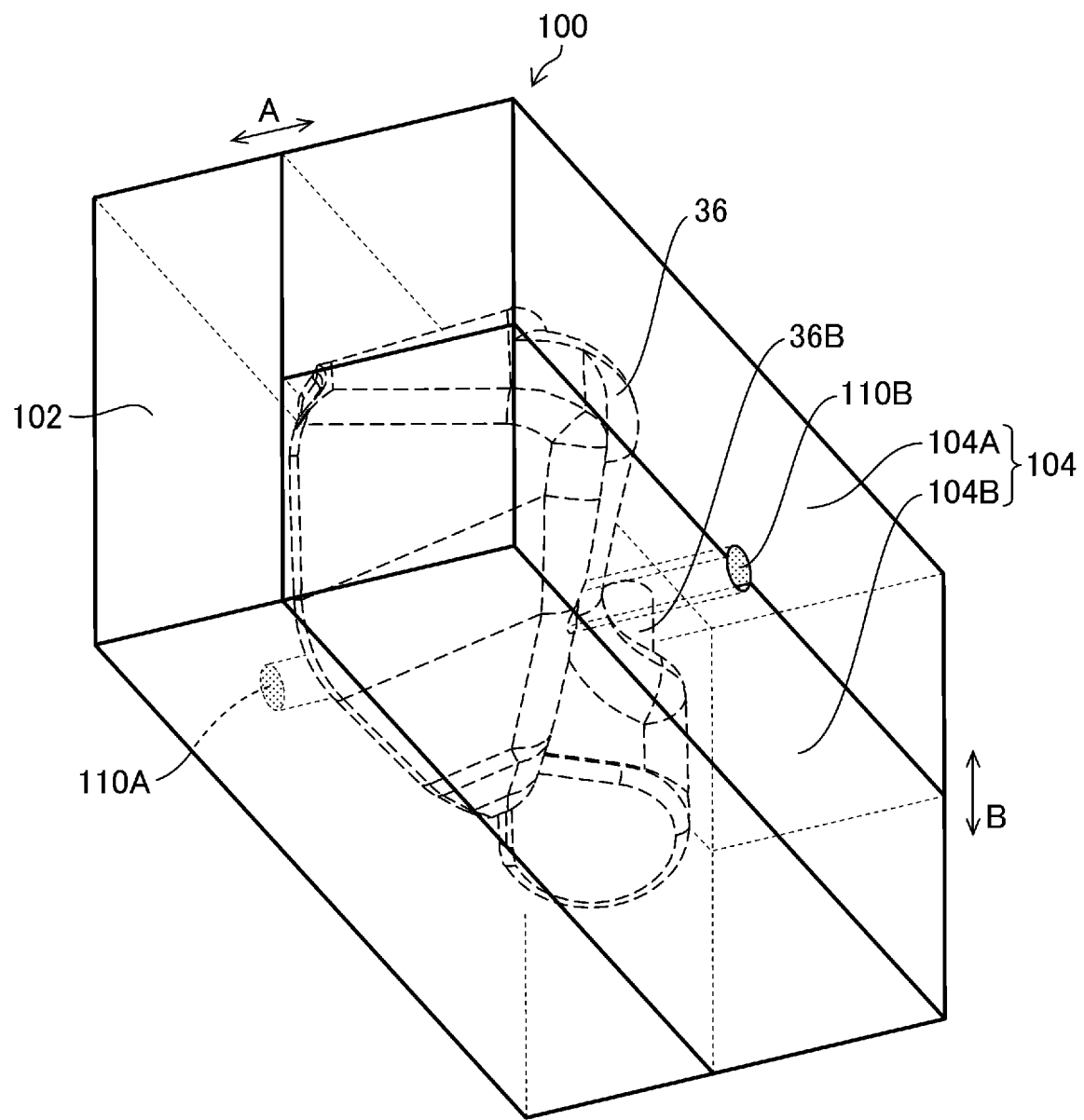
FIG. 11 is a perspective view of a die that is used in the method of molding an elevator according to the first embodiment.

FIG. 11 is a perspective view of the die 100. Preferably, the first die 102 and the second die 104 may be separated in the separation direction A at a position passing through the center (axis) of the rotation shaft 36B of the elevator 36. By setting the separation position of the first die 102 and the second die 104 at the center of the rotation shaft 36B, it is possible to easily separate the first die 102 and the second die 104 with respect to the elevator 36 having the rotation shaft 36B.

The separation position of the first die 102 and the second die 104 is not limited to a position passing through the center of the rotation shaft 36B, the center of the rotation shaft 36B may be located on the second die 104 side, and the die 100 may be designed so that the rotation shaft 36B is disposed on the second die 104 side. Because the second die 104 is separable in the separation direction B into the first member 104A and the second member 104B, it is possible to pull out the rotation shaft 36B from the second die 104 by separating the second die 104 in the separation direction B.

The separation position described above is a separation position of the first die 102 and the second die 104 in the case of integrally molding the rotation shaft 36B and the elevator 36. However, the rotation shaft 36B may be formed as an independent member, and a hole into which the rotation shaft 36B is to be inserted may be provided in the elevator 36. In the case of forming a hole in the elevator 36, a shaft member is provided at a position in the second die 104 corresponding to the hole in the elevator 36. Because the second die 104 is separable into the first member 104A and the second member 104B, it is possible to pull out the shaft member by separating the second die 104 and to form the hole. The shaft member for forming the hole need not be provided in the second die 104, and may be disposed in the cavity 106 as a member independent from the first die 102 and the second die 104. In the case where the shaft member for forming the hole is an independent member, the separation position of the first die 102 and the second die 104 is not particularly limited.

As in the method of molding an elevator according to the present embodiment, by making the wire-axis direction of the operation wire 40 and the separation direction A of the first die 102 and the second die 104 coincide with each other, it is possible to pull out the elevator 36 and the second die 104 in a state in which the first die 102 is fixed. By fixing the first die 102, it is possible to easily perform mating of the die. Moreover, because it is possible to continuously mold the elevator 36 in a state in which the operation wire 40 is constantly passed through the first die 102, it is possible to easily adjust the position of the operation wire 40. Accordingly, it is possible to easily perform continuous molding the elevator 36.

Because the treatment-tool guiding surface 36A has a recessed shape with respect to the wire-axis direction of the operation wire 40, it is possible to easily mold the treatment-tool guiding surface 36A into a shape that matches the shape of the contact member 37.

Second Embodiment

A method of molding an elevator according to a second embodiment is a method of molding elevators one by one.

Figure 12:
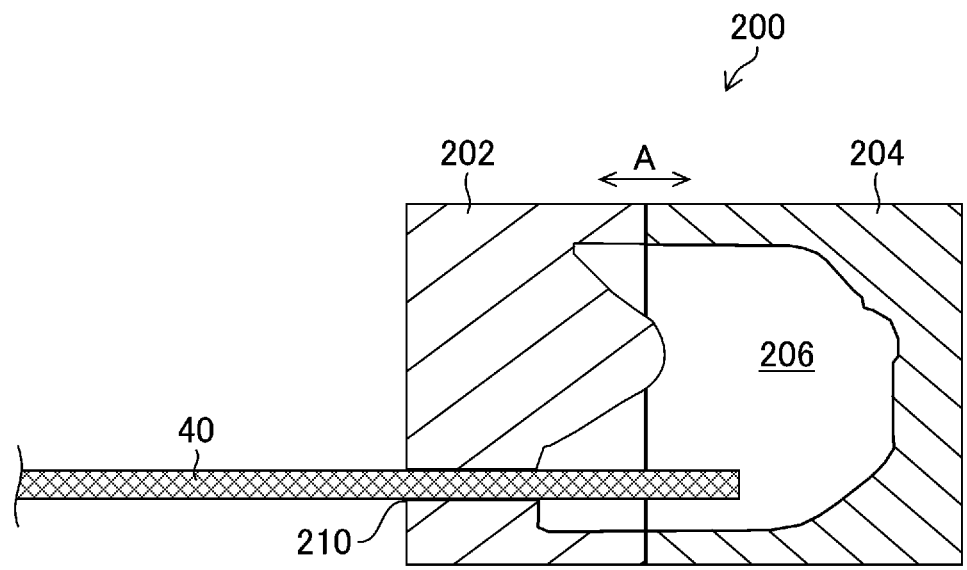
FIG. 12 illustrates a method of molding an elevator according to a second embodiment.
Figure 13:
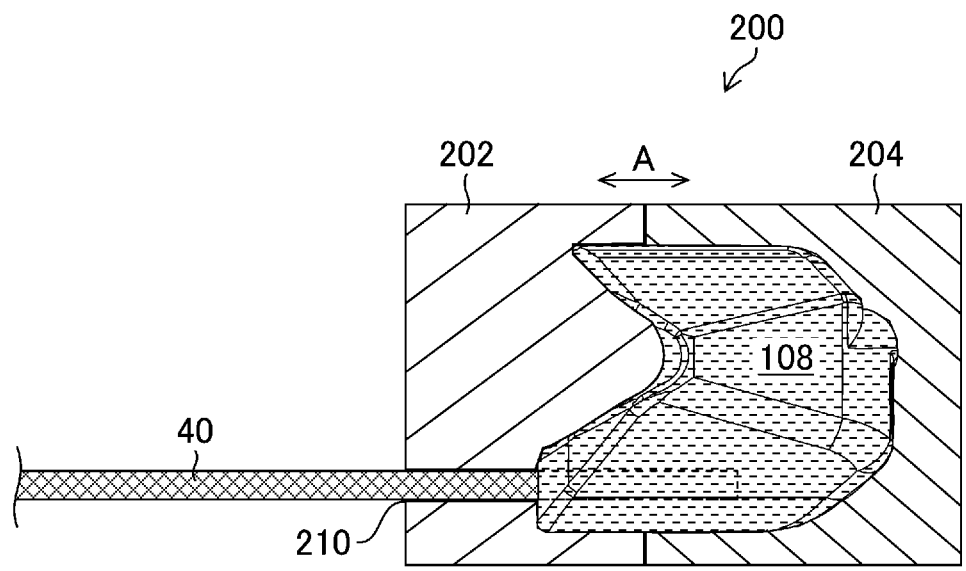
FIG. 13 illustrates the method of molding an elevator according to the second embodiment.
Figure 14:
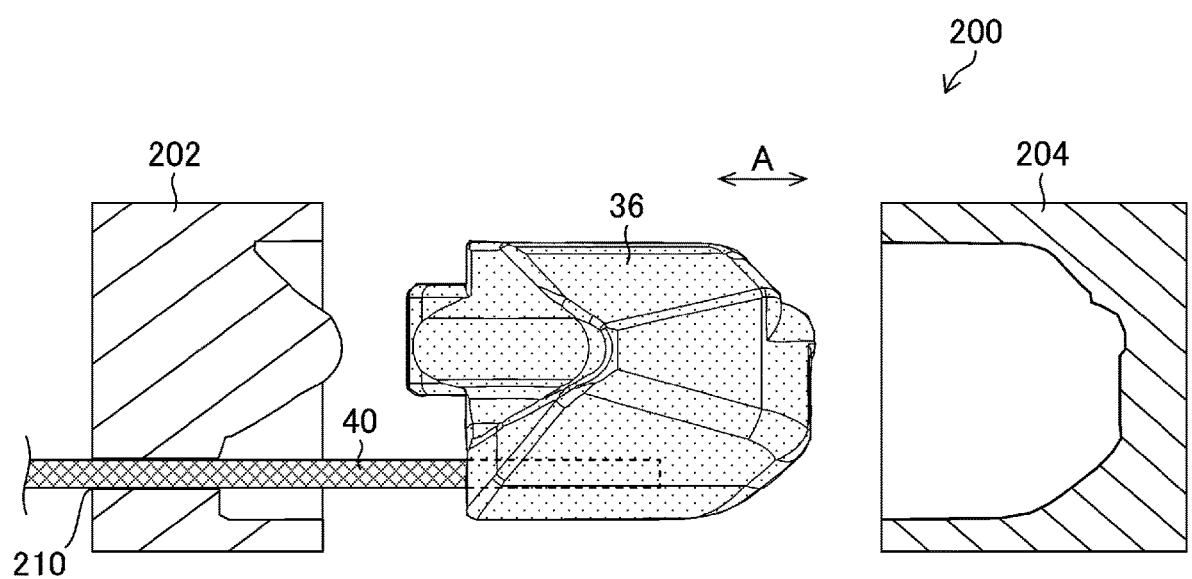
FIG. 14 illustrates the method of molding an elevator according to the second embodiment.

FIGS. 12 to 14 illustrate the method of molding an elevator according to the second embodiment, and are each a sectional plan view cut at the position of the operation wire 40. Because the method of molding an elevator according to the second embodiment is not continuous molding, the method differs from the method of molding an elevator according to the first embodiment in that, although a first die 202 and a second die 204 are separated, the second die 204 is not separated. The structure of the inside of the cavity 206 of the first die 202 and the second die 204 is omitted for simplicity of the drawings.

Molding of the elevator is performed by using a die 200 that is composed of the first die 202 and the second die 204. By mating the first die 202 and the second die 204 to each other, a cavity 206 corresponding to the elevator 36 is formed inside of the first die 202 and the second die 204. The first die 202 has a through-hole 210 for inserting the operation wire 40 into the cavity 206.

As illustrated in FIG. 12, when molding the elevator 36, first, the first die 202 and the second die 204 are mated. The operation wire 40 extends through the through-hole 210 provided in the first die 202, and the distal end of the operation wire 40 is disposed to extend into the cavity 206. At this time, the operation wire 40 is disposed so that the wire-axis direction of the operation wire 40 and the separation direction A of the first die 202 and the second die 204 coincide with each other.

Next, as illustrated in FIG. 13, the molding material 108, which is the material of the elevator 36, is injected into the cavity 206. A material similar to the material in the first embodiment ca be used as the molding material. After filling the cavity with the molding material 108, the molding material 108 is cooled to be solidified, and thus the elevator 36 in which the operation wire 40 is inserted is formed.

Lastly, the first die 202 and the second die 204 are separated in the separation direction A, and the elevator 36 is pulled out from the die 200. Because the separation direction A of the first die 202 and the second die 204 coincide with the wire-axis direction of the operation wire 40, it is possible to easily pull out the elevator 36 from the die 200 by separating the first die 202 and the second die 204 in the separation direction A.

Also with the present embodiment, it is possible to separate the elevator 36 and the second die 204 from the first die 202 by separating the second die 204 in the separation direction A in a state in which the first die 202 is fixed. It is possible to pull out the operation wire 40 from the die 200 by pulling out the elevator 36 in the separation direction A of the die 200.

In the case of integrally molding the elevator 36 and the rotation shaft 36B, the separation position of the first die 202 and the second die 204 is a position passing through of the center (axis) of the rotation shaft 36B. In the case of using an independent member as the rotation shaft 36B and providing a hole for inserting the rotation shaft 36B, preferably, a shaft member for forming the hole may be disposed as an independent member, in addition to the first die 202 and the second die 204.

Third Embodiment

A method of molding an elevator according to a third embodiment, which is a method of continuously molding an elevator, differs from the methods of molding an elevator according to the first embodiment and the second embodiment in that the separation direction A of the first die and the second die is a direction perpendicular to the wire-axis direction of the operation wire 40.

Figure 15:
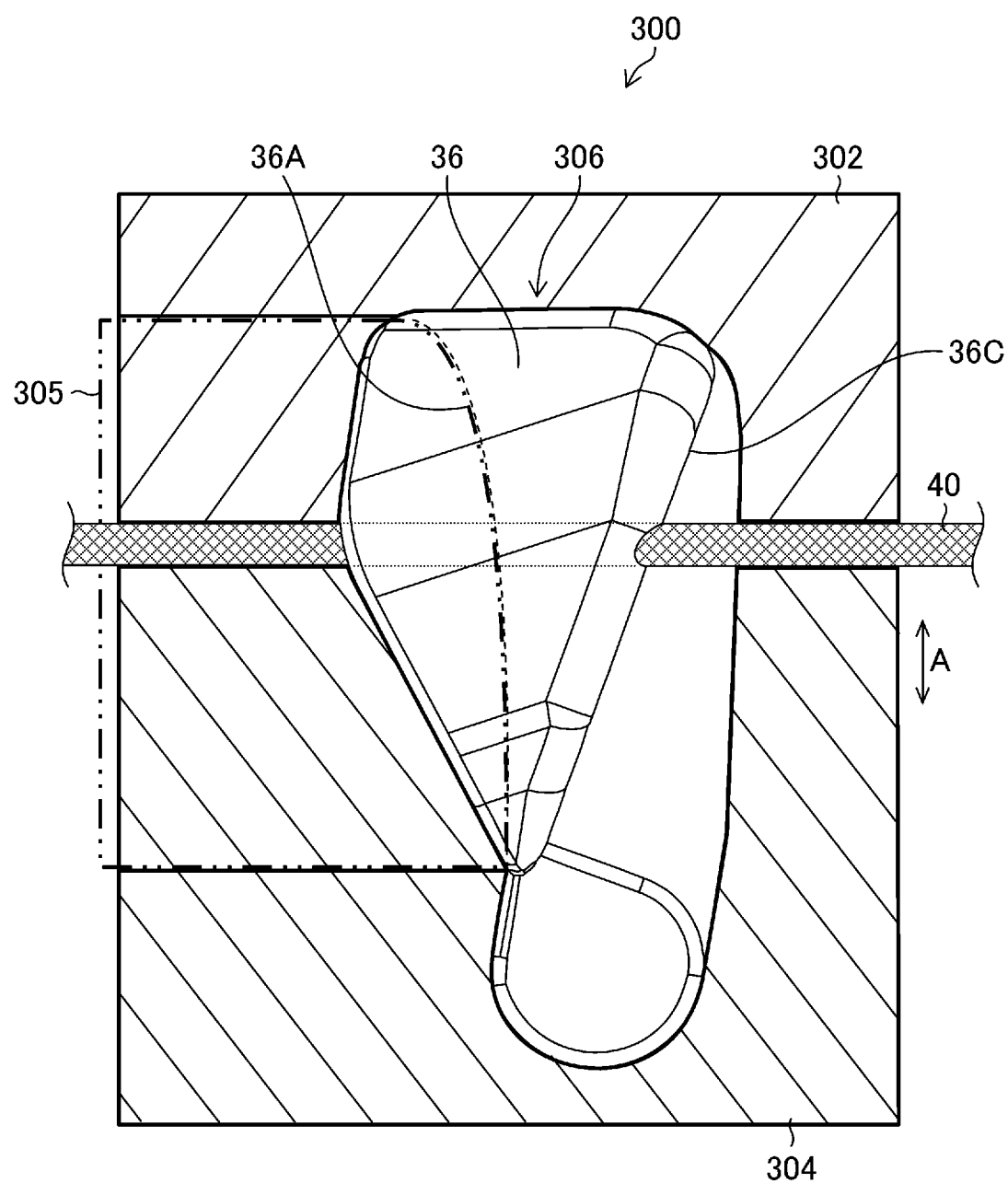
FIG. 15 is a side sectional view of a die that is used in a method of molding an elevator according to a third embodiment.
Figure 16:
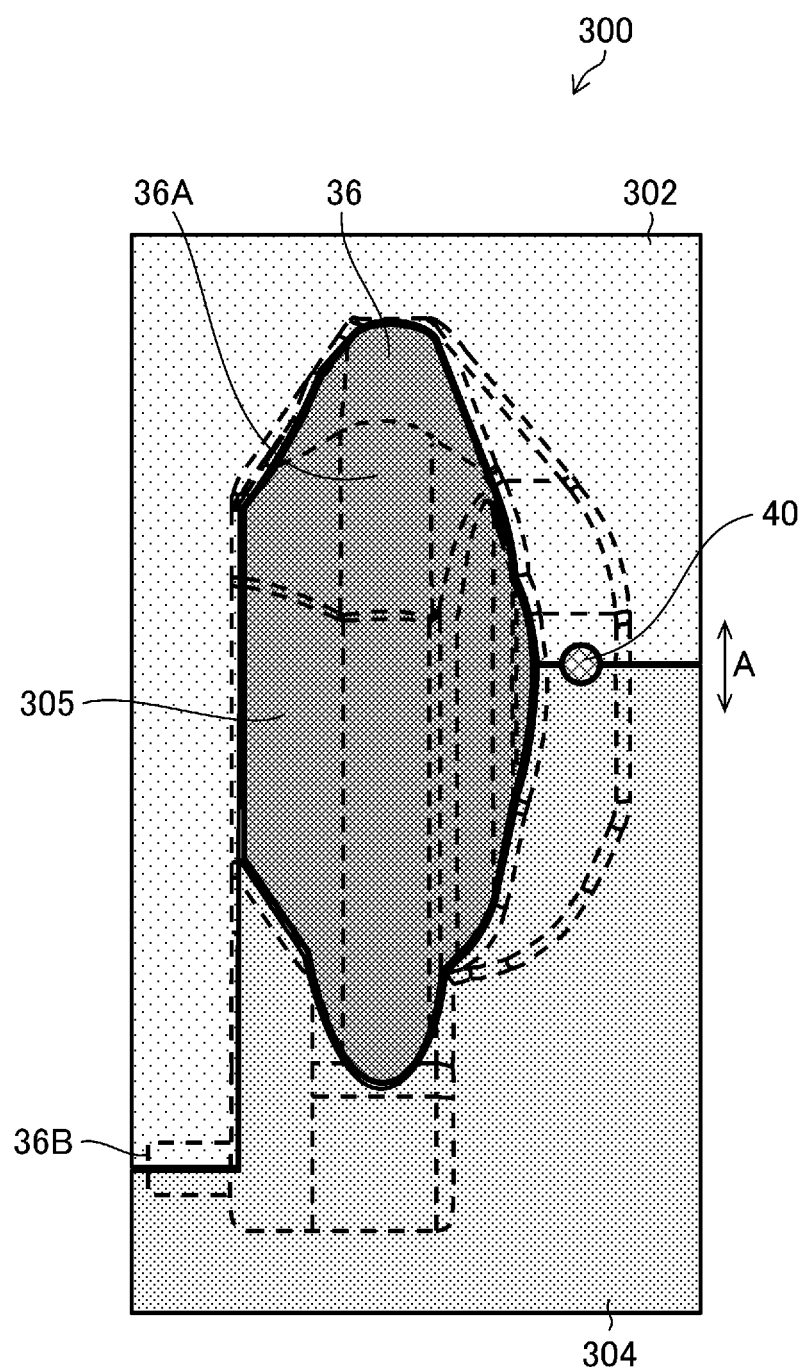
FIG. 16 is a schematic view illustrating the positional relationship between the separation position of the die and the elevator.

FIG. 15 is a side sectional view of a die used in the method of molding an elevator according to the third embodiment. FIG. 16 is a schematic view illustrating the positional relationship between the separation position of the die and the elevator, as seen from the wire-axis direction of the operation wire. In FIG. 16, the elevator 36 molded in a die 300 is shown by a see-through line (dotted line).

The die 300 used in the method of molding an elevator according to the third embodiment is composed of a first die 302 and a second die 304. The first die 302 and the second die 304 are separable in the separation direction A with respect to the wire-axis direction of the operation wire 40. As illustrated in FIG. 16, the die 300 has a guiding-surface forming member 305 for forming the treatment-tool guiding surface 36A of the elevator 36. By providing the guiding-surface forming member 305, it becomes easy to form the treatment-tool guiding surface 36A to have a desirable shape that can easily guide a treatment tool or a shape that matches the shape of the contact member 37.

When molding the elevator 36, the first die 302 and the second die 304 are mated, and the guiding-surface forming member 305, for forming the treatment-tool guiding surface 36A of the elevator 36, is further mated to form a cavity 306. As illustrated in FIG. 16, the operation wire 40 is inserted into a space between the first die 302 and the second die 304. That is, the operation wire 40 is inserted into the cavity 306, in a state in which a direction perpendicular to the separation direction A of the first die 302 and the second die 304 and the wire-axis direction of the operation wire 40 coincide with each other. After the operation wire 40 has been disposed in the cavity 306, the cavity 306 is filled with a molding material. After filling with the molding material, the molding material is cooled to be solidified, and thus the elevator 36 in which the operation wire 40 is disposed is formed.

Figure 17:
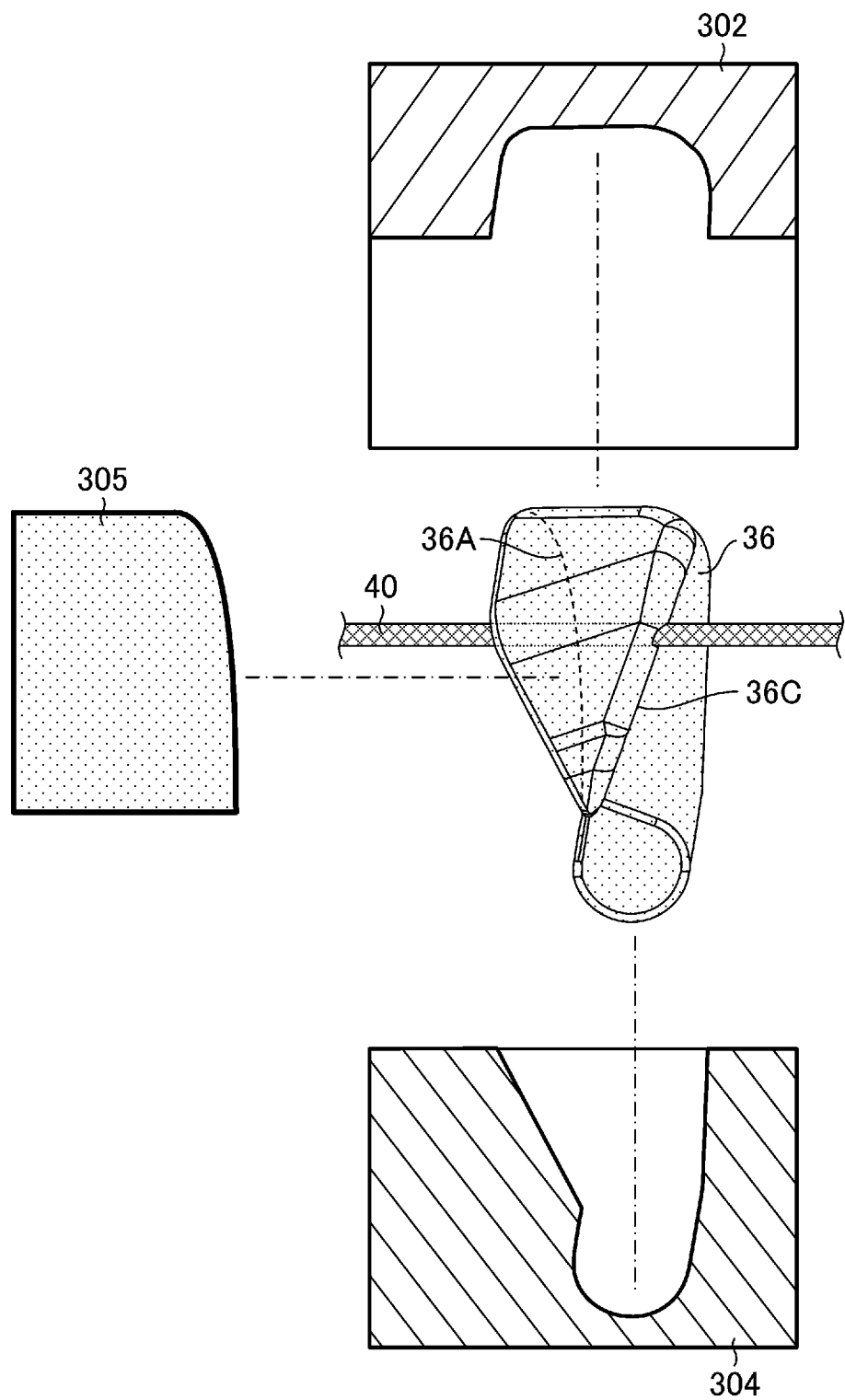
FIG. 17 is an exploded view of the die that is used in the method of molding an elevator according to the third embodiment.

After forming the elevator 36, as illustrated in FIG. 17, the first die 302 and the second die 304 are separated in a separation direction perpendicular to the axial direction of the operation wire 40, and the guiding-surface forming member 305 is slid in a direction parallel to the axial direction of the operation wire 40. The molded elevator 36 can be pulled out from a space between the first die 302 and the second die 304 that have been separated in the separation direction A.

After pulling out the elevator 36 from the die 300, the first die 302, the second die 304, and the guiding-surface forming member 305 are mated to each other again. The cavity 306 of the mated die 300 is filled with a molding material, and continuous molding of the elevator 36 is performed.

As in the molding method according to the first embodiment, a part of the operation wire 40 on the treatment-tool guiding surface 36A side is cut to have a length connectable with the elevating operation lever 20. The operation wire 40 protruding from the back surface 36C side is cut along the back surface 36C.

As illustrated in FIG. 16, the first die 302 and the second die 304 of the die 300 used in the method of molding the elevator 36 according to the third embodiment is separated at the position of the operation wire 40 and the position of the rotation shaft 36B. Thus, it is possible to separate the first die 302 and the second die 304 in a direction perpendicular to the axial direction of the operation wire 40.

The rotation shaft 36B may be a member independent from the elevator 36. In this case, in order to form a hole for inserting the rotation shaft 36B in the elevator 36, a shaft member for forming the hole is disposed in the cavity 306 to form the hole.

In the third embodiment, when taking out the molded elevator 36 from the die 300, it is necessary to move both of the first die 302 and the second die 304 in a direction perpendicular to the axial direction of the operation wire 40. Therefore, when mating the first die 302 and the second die 304 to each other, it is necessary to align the operation wire 40.

Fourth Embodiment

Figure 18:
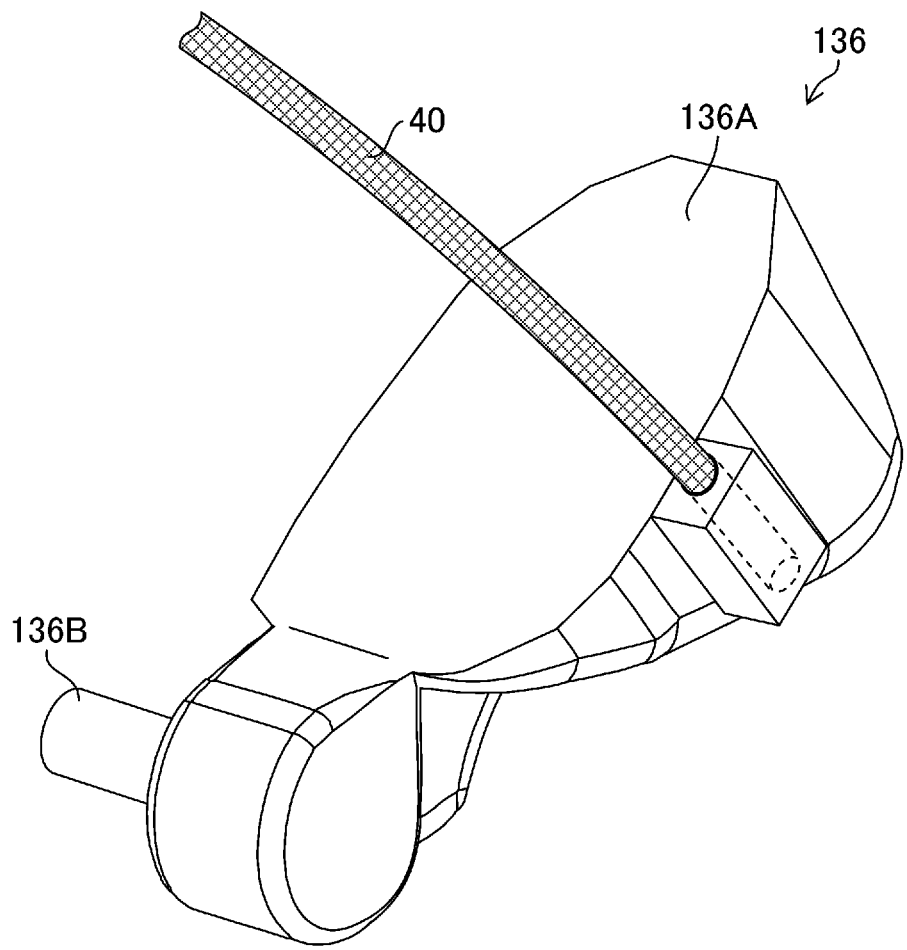
FIG. 18 is a perspective view of an elevator that is molded by using a method of molding an elevator according to a fourth embodiment.
Figure 18:
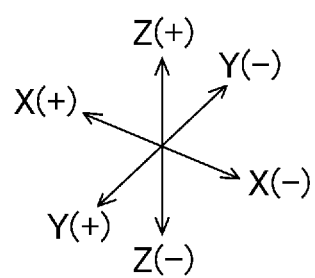
Figure 19:
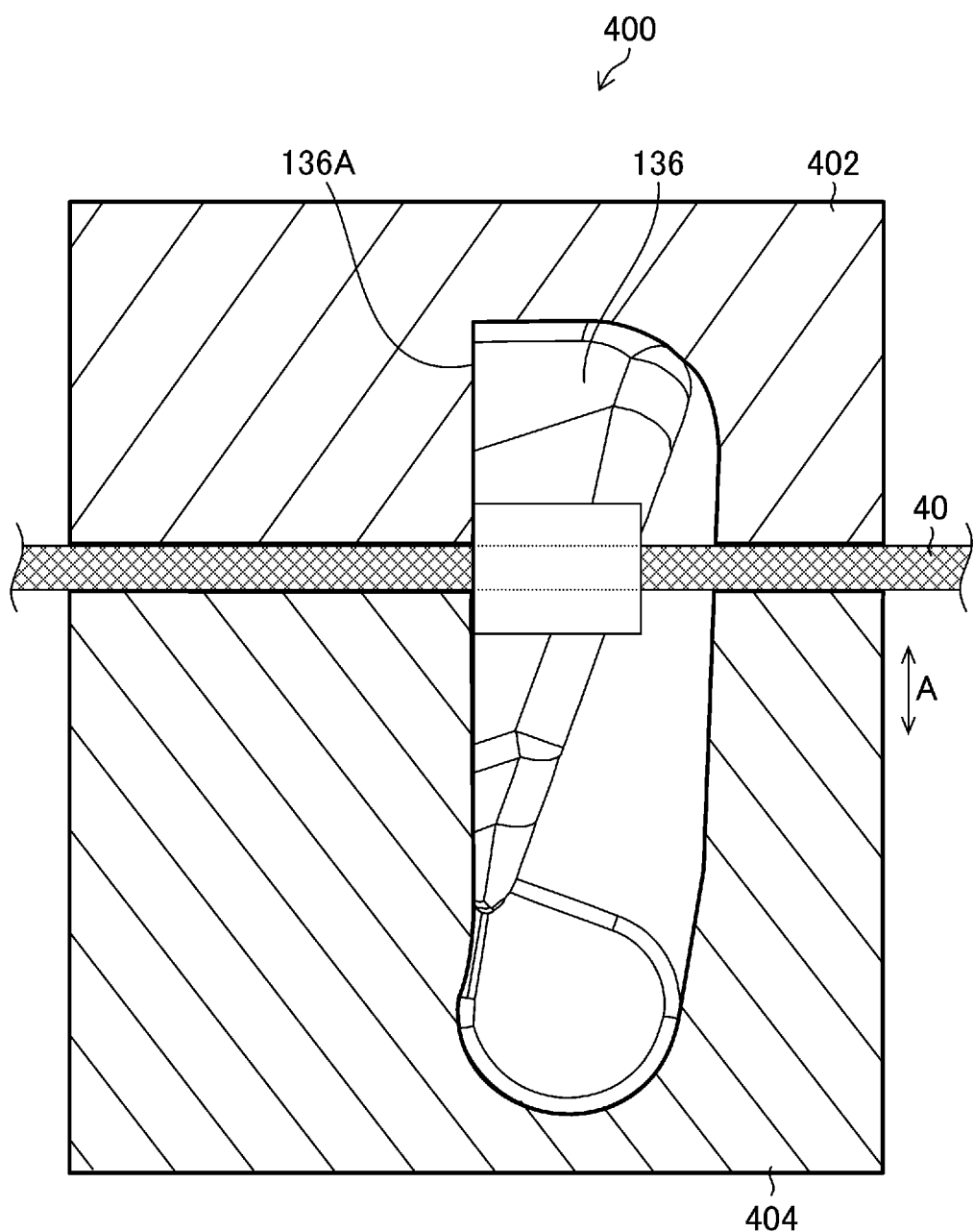
FIG. 19 is a side sectional view of the die that is used in the method of molding an elevator according to the fourth embodiment.
Figure 20:
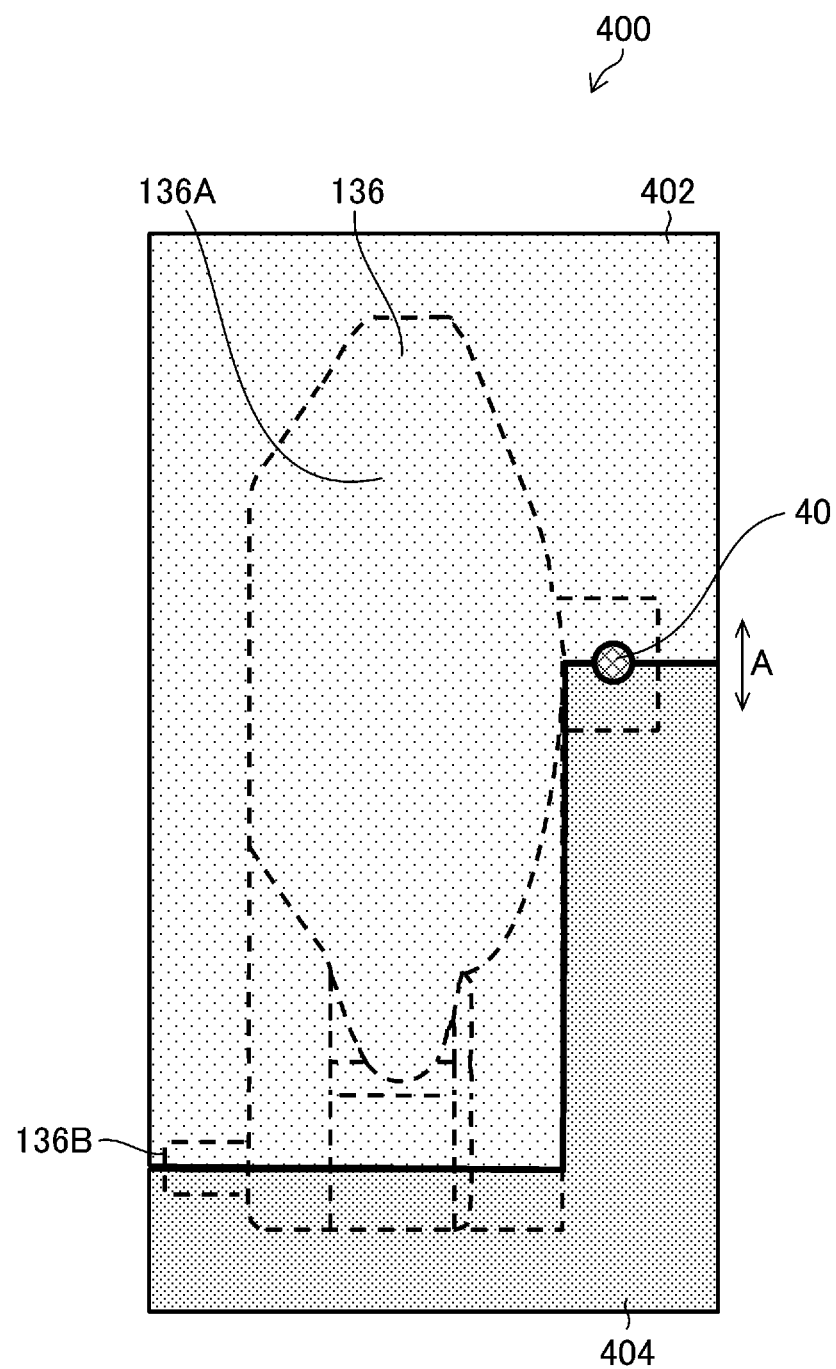
FIG. 20 is a schematic view illustrating the positional relationship between the separation position of the die and the elevator.

FIGS. 18 to 20 illustrate a method of molding an elevator according to a fourth embodiment. FIG. 18 is a perspective view of an elevator 136 molded by using the method of molding an elevator according to the fourth embodiment. Also in the method of molding an elevator according to the fourth embodiment, as in the method of molding an elevator according to the third embodiment, the elevator 136 is molded in a state in which the wire-axis direction of the operation wire 40 coincides with a direction perpendicular to the separation direction of a first die 402 and a second die 404. The elevator 136, which is molded by using the method of molding an elevator according to the fourth embodiment, differs from the elevator 36 illustrated in FIG. 5 in that a treatment-tool guiding surface 136A is a flat surface.

In the method of molding an elevator according to the fourth embodiment, because the treatment-tool guiding surface 136A is not a recessed curved portion but is a flat surface, it is possible to mold the elevator 136 without providing the guiding-surface forming member 305, which is used in the molding method according to the third embodiment. That is, in the molding method according to the fourth embodiment, it is possible to mold an elevator by using a die 400 composed of two members, which are the first die 402 and the second die 404.

FIG. 19 is a side sectional view of the die used in the method of molding an elevator according to the fourth embodiment, and FIG. 20 is a schematic view illustrating the positional relationship between the separation position of the die and the elevator as seen from the wire-axis direction of the operation wire. In FIG. 20, the elevator 136 molded in the die 400 is shown by a see-through line (broken line).

The first die 402 and the second die 404 are separated at the position of the operation wire 40 and a rotation shaft 136B. Thus, it is possible to separate the first die 402 and the second die 404 in a direction perpendicular to the axial direction of the operation wire 40. Preferably, a portion corresponding to the treatment-tool guiding surface 136A is molded by using either of the first die 402 or the second die 404 so that a connection portion may not be formed at the treatment-tool guiding surface 136A of the elevator 136 to be molded. In FIG. 20, the treatment-tool guiding surface 136A is molded by using the first die 402. Because a connection portion is not formed at the treatment-tool guiding surface 136A, it is possible to smoothly guide a treatment tool led out from the treatment-tool lead-out port 60.

REFERENCE SIGNS LIST 10 endoscope
12 endoscope system
14 processor device
16 light source device
18 display
20 elevating operation lever
22 operation section
24 insertion section
26 flexible portion
28 bending portion
30 distal end portion
32 distal-end-portion body
34 cap
34A open window
34B wall portion
34C bearing
36, 136 elevator
36A, 136A treatment-tool guiding surface
36B rotation shaft
36C back surface
36D connection portion
36E exposed portion
37 contact member
40 elevating operation wire
42 air/water supply tube
46 operation section body
48 grip portion
50 breakage preventing tube
52 universal cable
54 light source connector
56 electric connector
57 air/water supply button
58 air/water supply nozzle
59 suction button
60 treatment-tool lead-out port
61 through-hole
62 angle knob
63 stopper portion
64 treatment-tool insertion port
66 elevator housing space
68 partition wall
68A upper surface
72 optical-system housing chamber
74 illumination window
76 observation window
100, 200, 300, 400 die
102, 202, 302, 402 first die
104, 204, 304, 404 second die
104A first member
104B second member
106, 206, 306 cavity
108 molding material
110A, 110B, 210 through-hole
305 guiding-surface forming member
A, B separation direction
Ax longitudinal axis of insertion section

What is claimed is:

1. A method of molding an elevator integrally with an operation wire, the elevator to be disposed so as to be rotatable around a rotation shaft and disposed in a distal-end-portion body provided on a distal end side of an insertion section of an endoscope, the method comprising:
a step of mating a first die that has a first groove part for forming one part of the elevator on one side in a direction of the rotation shaft to a second die that has a second groove part for forming another part of the elevator on another side opposite to the one side in the direction of the rotation shaft, and disposing the operation wire to extend through a cavity formed by the first die and the second die in a state where a separation direction in which the first die and the second die are separable from each other, coincides with a wire-axis direction of the operation wire;

a step of integrally molding the elevator and the operation wire by injecting a molding material, which is a material of the elevator, into the cavity; and a step of separating the first die and the second die in the separation direction after molding the elevator.

2. The method of molding an elevator according to claim 1, wherein the elevator has a treatment-tool guiding surface and a back surface that is disposed on a side opposite to the treatment-tool guiding surface, and wherein the method further comprises a step of cutting the operation wire protruding from the back surface side of the treatment-tool guiding surface after separating the first die and the second die.

3. The method of molding an elevator according to claim 1, wherein the molding material is a molten resin.

4. The method of molding an elevator according to claim 1, wherein the molding material is a molten metal, and wherein the cavity is filled with the molten metal by metal powder injection molding.

5. The method of molding an elevator according to claim 4, wherein a material of the operation wire is tungsten.

6. A method of molding an elevator integrally with an operation wire, the elevator to be disposed so as to be rotatable around a rotation shaft and disposed in a distal-end-portion body provided on a distal end side of an insertion section of an endoscope, the method comprising:

a step of mating a first die that has a first groove part for forming one part of the elevator on one side in which the rotation shaft is to be disposed to a second die that has a second groove part for forming another part of the elevator on another side opposite to the one side in which the rotation shaft is to be disposed, and disposing the operation wire to extend through a cavity formed by the first die and the second die in a state where a direction perpendicular to a separation direction in which the first die and the second die are separable from each other, coincides with a wire-axis direction of the operation wire;

a step of integrally molding the elevator and the operation wire by injecting a molding material, which is a material of the elevator, into the cavity; and a step of separating the first die and the second die in the separation direction after molding the elevator.

* * * * *